United States Patent [19]

Braun et al.

[11] 4,324,250

[45] Apr. 13, 1982

[54] BODY SLENDERIZING METHOD

[76] Inventors: Sam M. Braun; Beatrice Braun, both of 2 rue Recamier, 75007 Paris, France

[21] Appl. No.: 107,387

[22] Filed: Dec. 26, 1979

[30] Foreign Application Priority Data

Dec. 28, 1978 [FR] France ................ 78 36737

[51] Int. Cl.$^3$ ................................ A61N 7/00
[52] U.S. Cl. ................................ 128/395
[58] Field of Search ............ 128/24.1, 82.1, 207.21, 128/362, 399, 402, 293, 395, 367, 368; 8/DIG. 8; 424/184

[56] References Cited

U.S. PATENT DOCUMENTS

| | | | |
|---|---|---|---|
| 2,911,974 | 11/1959 | Spence | 128/293 |
| 3,307,554 | 3/1967 | Thornton et al. | 128/293 |
| 3,310,052 | 3/1967 | Ward, Jr. | 128/293 |
| 3,541,205 | 11/1970 | Hardigan et al. | 424/184 |
| 3,880,996 | 4/1975 | Fisher | 424/184 |

FOREIGN PATENT DOCUMENTS

| | | | |
|---|---|---|---|
| 2118203 | 7/1972 | France | 128/82.1 |
| 2260988 | 9/1975 | France | 128/293 |

OTHER PUBLICATIONS

Reilly; Silicones and Their Use in Aerosols; in Soap and Chemical Specialties; Feb. 1958, pp. 113–115, 119, 159.

*Primary Examiner*—Robert W. Michell
*Assistant Examiner*—Daniel P. Burke
*Attorney, Agent, or Firm*—Steinberg & Raskin

[57] ABSTRACT

A body slenderizing method is disclosed comprising topically applying on the body a composition comprising a silicon organic derivative in combination with heat notably under the form of infra-red rays.

14 Claims, No Drawings

BODY SLENDERIZING METHOD

The present invention essentially relates to a body slenderizing method and composition with the object to treat all or part of the body of a patient, so as to reach a general or localized body slenderizing.

The invention slenderizing method comprises topically applying on all or part of the body of a patient a composition comprising a silicon organic derivative in an amount ranging between 0.05 and 5 weight percent with a view to reach a general or localized body slenderizing, then covering and/or overlapping the treated zone with the aid of a fluid-tight flexible sheet, preferably coated with an isothermic layer, and applying thereafter heat onto said thus covered zone, notably under the form of infra-red rays, during a period of time ranging between 15 minutes and 45 minutes, preferably between 20 minutes and 40 minutes, and repeating said sequence of operations at each sitting period, in at least 10 sitting periods and preferably at least 20 sitting periods, at the rate of at least 1 sitting period per month and at most one sitting period per day, preferably at the rate of 2 to 4 sitting periods per week.

Advantageously, applying of heat is started a certain time before the coating with the slenderizing composition.

According to one specific feature of the invention, the method is performed, within a continuous treatment, in at least 10 sitting periods per year and preferably at least 20 sitting periods per year.

According to another feature of the invention method, infra-red rays lamps of about 300 to 500 watts each, located at about 60-90 cm from the body, are used the total power of said lamps being of the order of 300 to 3000 watts, according to the extent of the treated zone.

According to again another specific feature of the invention method for the treatment of the whole human body about 10 to about 20 g of said composition is used per sitting period or sequence of the above operations.

The present invention also relates to a slenderizing composition for topical application and subsequent treatment with calorific radiations comprising a silicon organic derivative in an amount ranging between about 0.05 to 5 percent by weight, said composition being notably in the form of an ointment based on an aqueous gel.

According to a preferred embodiment of said composition, the weight ratio of said organic derivative ranges between 0.1 and 2%.

According to another preferred embodiment of said invention composition, said silicon organic derivative is a silanol, namely a silane derivative comprising at least one hydroxy function (OH), said silanol being optionally substituted by one or several hydrocarbon groups; a particular example of such substituted silanol, of particularly advantageous use, is dimethylsilanol.

Due to the fact that a great number of derivatives of this type, under their active form as concerns their slenderizing effect, are unstable and have a tendancy to polymerize, the silicon organic derivative of the invention slenderizing composition is preferably used in intimate mixture, notably in the form of a solution, with a substance avoiding its polymerization, such a substance being for instance a mono- or poly-alcohol.

The invention slenderizing composition advantageously has an acid reaction, namely its pH is within a range characterizing a weak acid state, said pH being advantageously of the order of 5.5 to 6.5.

As previously emphasized, the amounts of slenderizing composition to be used are of the order of 10 to 20 g per sequence of operations, namely per sitting period, and this corresponds to the content of an usual tube for pommades or ointments.

The proper use of the invention slenderizing composition in accordance with the invention method, provides the following results:

slenderizing of the body form;

lowering of the extent and/or of the number of ungraceful rolls or folds of fat, and in most cases the full disappearance thereof;

better quality and flexibility of the body tissues located under the epidermis (dermis and hypodermis);

loss of weight (without trying to obtain said particular effect, an appreciable loss of body weight has been observed in some cases).

There is given here-below a non-limitative example of slenderizing composition according to the present invention.

EXAMPLE

| | |
|---|---|
| A solution comprising 5% of dimethylsilanol dissolved in hexylene-glycol | 10 g |
| Carboxyvinylic gel at 1.25% | 40 g |
| Methyl paraoxybenzoate (preservative) | 0.1 g |
| Propyl paraoxybenzoate (preservative) | 0.1 g |
| Caustic soda (NaOH) | sufficient amount to obtain a pH of about 5.6 |
| Solution at 5/1000 of methylrosaniline chloride in a sufficient amount to obtain a slightly parme coloration | |
| Purified water | to 100 g |

Said composition can be used to fill flasks or tubes containing about 10 to 15 cm$^3$ where the content represents about the amount of composition necessary for a sequence or series of operations, namely a treating sitting period of the whole of the human body.

Said composition can be in the form of an aqueous liquid or gel, colorless, with a slightly aromatic smell, having a specific gravity of 0.929 or in the form of a non-aqueous product, fluid or non-fluid containing notably a gel, for instance a carboxyvinylic gel.

Within the present invention, the pH of said composition can range between 5.5 and 6.5.

In the aforesaid given example of slenderizing composition, the formation of insoluble polysiloxanes within water, biologically inactive, through polycondensation of dimethylsilanol, is avoided by the formation of hydrogen type bonds with the alcohol functions of hexylene-glycol.

Applicants believe that the slenderizing composition according to the present invention acts through a qualitative effect of restructuration of mucopolysaccharides and of collagene of conjunctive tissues located under the epidermis and having been injured through a processus of "localized fattening" and that this effect is highly magnified with the treatment with the aid of calorific radiations, after topical application of the slenderizing composition.

As already mentioned, according to the present invention there can be advantageously used an infra-red ray during the heat treatment step of the selected zone of the body.

The infra-red ray can be given by an infra-red ray lamp or a series of lamps of a total power ranging between 300 and 3000 watts and this, according to the extent of the treated zone; individual lamps, preferably of a power of about 300 to 500 watts, are located at about 60-90 cm from the body.

There can be used:

either infra-red ray lamps with individual reflectors and with circuit breakers independent one from the other, so as to order separately said reflectors, if necessary;

or modern "sunny bands" allowing to direct onto the treated body of the patient an infra-red ray having a band of wave lengths well defined, or a mixed ray infra-red+ultraviolet, in no case however, do ultraviolet ray lamps have to be used;

or one or several lamps fully independent one from the other, where the rays are conducted, either directly or indirectly, (for instance with the aid of reflectors) onto the body of the patient.

The patient to be treated can be either seated, or standing, or lying, or in any other position for the treatment according to the invention method; the lying position is however preferred.

EXAMPLE OF TREATMENT WITH INFRA-RED RAY

The patient lies elongated, naked on an horizontal plane (bed, relaxing chair put in elongated position, kinesitherapeutical massing table, mattress on low side, and so on);

one sheet of fluid-tight impervious plastic material, very fine, of about 150 cm × 150 cm is located under the patient;

the infra-red ray lamps are located at about 70-80 cm from the body, according to their power (the 300 watt lamps being located nearer the body than the 500 watt lamps);

the patient being thus positioned, the body is submitted to the calorific ray during 10 minutes.

after this period of time, without switching off the lamps, there is spread onto the body, with the hand, or with the aid of a glove, the total content of a flask or a tube (about 10 to 15 cm$^3$) of slenderizing composition, said operation being carried out quite quickly since the slenderizing composition has a certain volatility; it should be noted that said composition is only applied onto the zones of the body where it is desired to obtain the wished for slenderizing;

the body of the patient or the zone thereof to be treated is bound up with the said plastic material sheet; the thighs or legs are notably overlapped independently one from the other with said sheet by folding back the sides of said plastic material sheet according to the internal sides of the thighs or legs;

the patient, thus overlapped with said plastic material sheet is coated with one isothermic layer constituted by a wool covering or another insulating material or, preferably an isothermic cover; the patient thus disposed is then submitted, during a period of time of about 20 minutes, to the action of the calorific ray of said lamps, so that the total exposure time of said ray is of the order of 1.2 hours;

by the end of the sitting period, the subject is wiped rather than given a shower.

The use of said fluid-tight plastic material sheet has essentially the object of avoiding vaporization of the volatile constituents of the slenderizing composition.

EXAMPLE OF TREATMENT WITH THE AID OF ANOTHER SOURCE OF CALORIFIC RAYS

Instead of using the ray given by infra-red ray lamps, a heat source of the type given by a sudation tank of the type "sauna", the calorific ray being applied onto one isolated part of the body or onto the whole part thereof is used. As in the preceeding case, after applying the slenderizing composition, a fluid-tight plastic material sheet is used.

TIME OF TREATMENT AND NUMBER OF SITTING PERIODS

There can be performed a treatment of determined time.

In all cases, at least 10 sitting periods and more, preferably at least 20 sitting periods, at the rate of at most 1 sitting period per day and at least 1 sitting period per month, preferably about 2 to 4 sitting periods per week are advantageously performed.

In the case of a continuous treatment, optionally for a period of several years, at least 10 sitting periods per year and preferably at least 20 sitting periods per year are performed, and this, during one undetermined period of time.

The frequency of the sitting periods is of course correlated to the family and professional life style of the patient.

It can be added that the slenderizing composition according to the present invention can be presented in any form and notably in the form of a cream, a gel, a foam, a lotion, a product for spraying or nebulisation, a soap, and so on.

Of course, the present invention is by no means limited to the forms of embodiment described and illustrated which have been given by way of example only. In particular, it comprises all means constituting technical equivalents to the means described as well as their combinations, should the latter be carried out according to its gist and used within the scope of the following claims.

What is claimed is:

1. Method of body slenderizing, which comprises topically applying on all or part of the body of a patient a composition comprising an unpolymerized silanol in intimate mixture with a substance preventing its polymerization, said silanol being in an amount ranging from about 0.05 and 5 weight percent, covering the treated zone with a fluid-tight flexible sheet, applying heat onto the covered zone during a period of time ranging between 15 minutes and 45 minutes, repeating this sequence of operations at each sitting period, in at least 10 sitting periods at the rate of at least 1 sitting period per month and at most one sitting period per day.

2. Method of claim 1, wherein the fluid-tight flexible sheet is coated with an isothermic layer.

3. Method of claim 1, wherein said heat is applied during a period of time ranging between 20 minutes and 40 minutes.

4. Method of claim 1, wherein the treatment is performed in at least 20 sitting periods.

5. Method of claim 1, wherein at least 2 to 4 sitting periods per week are utilized.

6. Method of claim 1, wherein the heat is applied by means of infra-red ray lamps of about 300 to 500 watts each, located at about 60-90 cm from the body, the total power of said lamps being of the order of 300 to 3000 watts according to the extend of the treated zone.

7. Method of claim 1 wherein for the treatment of the whole body from about 10 to about 20 g of said composition is used per sitting period or per said sequence of operations.

8. Method of claim 1, wherein heat is applied to the body zone prior to the application of said composition.

9. Method according to claim 1 wherein said silanol is dimethyl silanol.

10. Method according to claim 1 wherein said substance which prevents polymerization is an alcohol.

11. Method according to claim 9 wherein said substance preventing polymerization is an alcohol.

12. Method according to claim 10 wherein said substance is hexylene glycol.

13. Method according to claim 11 wherein said substance is hexylene glycol.

14. Method according to claim 9 wherein said heat is applied by infra-red rays.

* * * * *